United States Patent
Smith et al.

(10) Patent No.: US 6,881,760 B1
(45) Date of Patent: Apr. 19, 2005

(54) METHODS FOR MONITORING SOLIDS CONTENT IN FISCHER-TROPSCH PRODUCTS

(75) Inventors: Ben Smith, Vacaville, CA (US); Richard Aviani, Pinole, CA (US); Dennis J. O'Rear, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 10/892,163

(22) Filed: Jul. 16, 2004

(51) Int. Cl.$^7$ ............................ C07C 27/00; G01J 5/02; G01J 3/36; G01T 1/20; G01N 21/00
(52) U.S. Cl. ............... 518/728; 250/341.1; 250/363.01; 356/307; 356/442
(58) Field of Search ....................... 518/728; 250/341.1, 250/353.01; 356/307, 442

(56) References Cited

U.S. PATENT DOCUMENTS 5,088,833 A * 2/1992 Tsang et al. .................. 374/17
5,090,817 A * 2/1992 Ker et al. ..................... 374/24

* cited by examiner

*Primary Examiner*—J. Parsa
(74) *Attorney, Agent, or Firm*—Burns, Doane, Swecker & Mathis, L.L.P.

(57) ABSTRACT

A method for monitoring the solids content in a Fischer-Tropsch product to allow subsequent changes in the Fischer-Tropsch process to prevent downstream problems. The method comprises irradiating the Fischer-Tropsch product with light and measuring the light transmitted through the Fischer-Tropsch product to determine the solids content in the Fisher-Tropsch product.

20 Claims, No Drawings

METHODS FOR MONITORING SOLIDS CONTENT IN FISCHER-TROPSCH PRODUCTS

FIELD OF THE INVENTION

The present invention relates to monitoring the solids content in Fischer-Tropsch products. In particular, the present invention relates to monitoring the solids content in Fischer-Tropsch products using optical techniques.

BACKGROUND OF THE INVENTION

Solids in Fischer-Tropsch products can cause problems in downstream operations. Solids can cause rapid wear in pumps, exchangers, process lines, and other equipment, as well as accumulate in downstream hydroprocessing units. An unacceptable level of solids in the products can also render the products non-salable.

The Fischer-Tropsch process is well known in the art. It is believed the most efficient method of converting natural gas into salable products, and the most efficient of them is catalysis in a slurry bed.

Slurry-bed Fischer-Tropsch processes and reactors are well known and documented in the literature, including, by way of example, U.S. Pat. Nos. 5,157,054, 5,763,716, and 5,776,988. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. Slurry Fischer-Tropsch reactors produce a vapor phase and a higher molecular weight liquid stream. Another reactor design that closely simulates a slurry bed reactor is an ebullated bed reactor, such as that described, for example, in U.S. Pat. No. 5,776,988. In the ebullated bed reactor, the catalytic bed is expanded and fluidized by means of a sufficiently high gas flow. No liquid phase is fed or recycled into the reaction section apart from the reaction products. The reactor also produces a vapor phase and a liquid stream as products.

While solids are not typically present in the vapor phase, when reactor hydrodynamics are unstable, it is possible for a portion of the liquid contents of the reactor, which may contain solids, to exit the reactor with the vapor phase. A "freeboard" zone, as described, for example, in U.S. Pat. No. 5,961,933, can be used to permit disengagement of the catalyst and the gaseous products. To prevent solids from exiting a Fischer-Tropsch reactor with liquid products and contaminating the final product, however, a separation device is typically used. While the separation device typically is a filter, other devices, including magnetic separators and extractors, can also be used.

For example, U.S. Pat. No. 5,827,903 discloses a Fischer-Tropsch slurry synthesis wherein the wax product along with dispersed catalyst is removed from the reactor slurry and purified by removing substantially all of the catalyst prior to upgrading the wax product. Separation of the catalyst particles from the wax product is accomplished by dense gas and/or liquid extraction. U.S. Pat. No. 5,387,340 discloses a wire filter element and a method of manufacturing the wire filter element, which element can be used for fine particle retention in catalyst reactions. Also, U.S. Pat. No. 5,527,473 discloses a process for performing reactions in a liquid-solid catalyst slurry where feed gases pass continuously upward through a slurry bed contained in a reactor vessel, convening the gases to liquid and vaporous products, and withdrawing the liquid products through a shaped-wire filter having slit openings. The filter element retains in the bed the solid catalyst particles larger than the slit width. U.S. Pat. Nos. 5,407,644 and 5,422,375 disclose separating a liquid product from the remainder of a reaction slurry which includes the product and a finely divided catalyst by means of a filter unit including a filter member.

However, separation devices are not always completely reliable, especially during upsets, and when solids are found present in Fischer-Tropsch products, the dirty product must be disposed of and the facility must be shut down for cleaning, otherwise problems in downstream operations can occur. If the presence of unacceptable amounts of solids in the Fischer-Tropsch process is not detected immediately, as mentioned earlier, the solids can cause rapid wear in pumps, exchangers, process lines, and other equipment. Accumulation in downstream hydroprocessing units can also occur. Of great interest to the industry, therefore, would be a Fischer-Tropsch process which can avoid the problems of unacceptable solids content in Fischer-Tropsch products and the inefficiencies and waste caused thereby. What is needed, therefore, is a method for effectively monitoring and/or controlling the solids content in Fischer-Tropsch products. More particularly, what is needed is a method of immediate response to an unacceptable solids content in Fischer-Tropsch products.

The interaction of radiation with matter has been discussed in U.S. Pat. No. 4,628,204. Measurement of the pour and cloud points of oil by detecting light scattering through the oil is known. For example, U.S. Pat. No. 5,088,833 discloses an apparatus for monitoring the cloud point of a liquid, or the temperature at which any light scattering phase occurs therein. U.S. Pat. No. 5,090,817 relates to an apparatus and process for estimating the pour point of a hydrocarbon oil.

Light scattering can also be used as a measure of the particle size of solids in a stream, as described in *Techniques of Chemistry. Vol. 1, Part IIIA. Physical Methods of Chemistry*, edited by Arnol Weissberger and Bryant Rossiter, Wiley-Interscience, New York, Chapter II written by Gerald Oster; *Absorption and Scattering of Light by Small Particles*, by Craig Bohren and Donald Huffman, Wiley-Interscience, New York, Chapter 14; and *Measurement of Suspended Particles by Quasi-Elastic Light Scattering*, edited by Barton Dahneke, Wiley-Interscience, New York. The primary use of light scattering is to determine particle size distribution.

While radiating streams with light has been used for the measurement of various properties, the successful use of light transmitting techniques to monitor/control a Fischer-Tropsch process has heretofore not been explored or achieved.

SUMMARY OF THE INVENTION

The present invention provides a process which allows one to effectively monitor and control the solids content in Fischer-Tropsch products. This is accomplished by using optical techniques. In one embodiment of the present invention, there is provided a method for monitoring the solids content in a Fischer-Tropsch product, the product being derived from a Fischer-Tropsch process comprising a Fischer-Tropsch reactor, comprises irradiating the Fischer-Tropsch product with light. Light transmitted through the Fischer-Tropsch product is measured, which information can be used to determine the solids content in the Fischer- Tropsch product. Effective changes in the Fischer-Tropsch process can then be made to avoid an unacceptable solids content in the Fischer-Tropsch product.

Among other factors, the present invention is based upon the discovery that irradiation of a Fischer-Tropsch product with light can provide an accurate determination of the solids content of the Fischer-Tropsch product, and that this determination can be successfully employed in a Fischer-Tropsch process to avoid the serious problems which can arise from an unacceptable solids content in a Fischer-Tropsch product. Such problems include wasted products, accumulation of catalyst fines in downstream hydroprocessing units, downtime, as well as excessive wear in pumps, exchangers, and other equipment. The technique of the present invention allows one to successfully monitor the solids content of Fischer-Tropsch products, permit immediate, appropriate changes in the Fischer-Tropsch process, and thereby avoid the serious problems that can arise.

DETAILED DESCRIPTION OF THE INVENTION

The present invention is directed to methods for monitoring and controlling the solids content in Fischer-Tropsch products, and more particularly, to methods of immediate response to unacceptable solids content in Fischer-Tropsch products. According to the present invention, an unacceptable solids content in Fischer-Tropsch products can be detected by applying an optical monitoring system involving the irradiation of product samples with light, thereby permitting an immediate response to avoid downstream problems.

The phrase "derived from a Fischer-Tropsch process" means that the product, fraction, or feed originates from or is produced at some stage by a Fischer-Tropsch process. In the Fischer-Tropsch process a hydrocarbon asset is converted to synthesis gas. The hydrocarbon asset can be selected from the group consisting of coal, natural gas, petroleum, and combinations thereof. In the Fischer-Tropsch synthesis process, liquid and gaseous hydrocarbons are formed by contacting a synthesis gas (syngas) comprising a mixture of $H_2$ and CO with a Fischer-Tropsch catalyst under suitable temperature and pressure reactive conditions. The Fischer-Tropsch reaction is typically conducted at temperatures of about from 300 to 700° F. (149 to 371° C.), preferably about from 400 to 550° F. (204 to 228° C.); pressures of about from 10 to 600 psia (0.7 to 41 bars), preferably 30 to 300 psia (2 to 21 bars); and catalyst space velocities of about from 100 to 10,000 cc/g/hr, preferably 300 to 3,000 cc/g/hr.

The products may range from $C_1$ to $C_{200+}$ with a majority in the $C_5$ to $C_{100+}$ range. The reaction can be conducted in a variety of reactor types for example, fixed bed reactors containing one or more catalyst beds, slurry reactors, fluidized bed reactors, or combinations of different type reactors. Such reaction processes and reactors are well known and documented in the literature. Slurry Fischer-Tropsch processes, which is a preferred process in the practice of the present invention, utilize superior heat (and mass) transfer characteristics for the strongly exothermic synthesis reaction and are able to produce relatively high molecular weight, paraffinic hydrocarbons when using a cobalt catalyst. In the preferred slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred Fischer-Tropsch process is taught in EP0609079.

Suitable Fischer-Tropsch catalysts comprise one or more Group VIII catalytic metals such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known and illustrative, but nonlimiting examples may be found, for example, in U.S. Pat. No. 4,568,663.

The products from Fischer-Tropsch reactions performed in slurry bed reactors generally include a light reaction product and a waxy reaction product. The light reaction product (i.e., the condensate fraction) includes hydrocarbons boiling below about 700° F. (e.g., tail gases through middle distillates), largely in the $C_5$ to $C_{20}$ range, with decreasing amounts up to about $C_{30}$. The waxy reaction product (i.e., the wax fraction) includes hydrocarbons boiling above about 600° F. (e.g., vacuum gas oil through heavy paraffins), largely in the $C_{20+}$ range, with decreasing amounts down to $C_{10}$. Both the light reaction product and the waxy product are substantially paraffinic. The waxy product generally comprises greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins.

The Fischer-Tropsch process of the present invention generally comprises separating solids, such as catalyst fines, from the Fischer-Tropsch product. The separation may be accomplished by filtration, sedimentation, centrifugation, and/or extraction and may be accomplished either inside the Fischer-Tropsch reactor or outside the Fischer-Tropsch reactor.

Typically, hydroprocessing is used to upgrade Fischer-Tropsch products to remove undesirable impurities such as oxygenates and improve stability. Hydroprocessing is the reaction of a hydrocarbonaceous feed with hydrogen over a catalyst at elevated temperature and pressure. The broad category of hydroprocessing can be divided into hydrotreating and hydrocracking. In hydrotreating, the goal is to remove heteroatoms, saturate olefins, saturate aromatics while minimizing the conversion to lower molecular weight species. As previously explained, among the problems that can arise from an unacceptable solids content in a Fischer-Tropsch product is accumulation of solids in hydroprocessing units.

It has been discovered that optical techniques based on light absorption, light scattering, and combinations thereof, may be used to successfully and accurately monitor the solids content in Fischer-Tropsch products. The term "light" as used herein means electromagnetic radiation in the infrared, visible, or ultraviolet range of the spectrum. Light transmitted through the Fischer-Tropsch product is measured to determine the solids content in the Fischer-Tropsch product. Measurement of light transmitted through the Fischer-Tropsch product may refer to measuring a reduction in light transmitted through the product due to absorption or measuring the scattering of light through the product.

Calibration of the measurement allows for determination of the solids content of the sample within a desired degree of accuracy. The solids present in Fischer-Tropsch products may comprise solids from the Fischer-Tropsch process such as catalyst fines or solids present in the feed to the Fischer-Tropsch process.

Preferably, the measurement is an on-line analysis. That is, the measurement is done directly in the process streams and provides a continuous measurement of the solids content. Alternatively, the measurement may be an off-line analysis, done on a sample removed from a process stream. Among the streams that may be monitored according to the methods of the present invention are liquid products derived from vapor streams from a Fischer-Tropsch reactor, liquid or wax products from a Fischer-Tropsch reactor, feedstocks to hydroprocessing units downstream of a Fischer-Tropsch reactor, and products from hydroprocessing units downstream of a Fischer-Tropsch reactor.

The process units that are downstream of the Fischer-Tropsch system are typically hydroprocessing units. These units can have serious problems with plugging from solids. It is important to maintain the solids content of streams fed to these units below certain predetermined levels. Visual observation might be used to determine the presence of solids, but visual observation is not quantitative, and waxy Fischer-Tropsch samples may solidify during analysis.

The optical techniques of the present invention are run on samples kept above the cloud point of the sample, preferably at least about 10° C. above the cloud point of the sample. "Cloud point" refers to the temperature at which wax first becomes visible when the sample is cooled under standardized test conditions (ASTM D2500). Further, the optical techniques of the present invention should be run on water-free samples, as water present in the sample may provide false readings of solids. Similarly, the sample should be free of gas bubbles, as gas bubbles present in the sample may provide false readings of solids.

Furthermore, if solids make their way through the downstream units, the solids can appear in the final products. When this happens, there is the danger that the solids in the product will cause damage to the customer's equipment, e.g., engine, turbine, machinery. Thus, analysis of the solids content from the hydroprocessing unit, perhaps at an even lower level, may be desirable.

Generally, it is preferred that the amount of solids in a product stream downstream of a Fischer-Tropsch reactor is less than 100 ppm, preferably less than 50 ppm solids, more preferably less than 10 ppm solids, and most preferably less than 1 ppm. Thus, an unacceptable solids content, i.e., a solids content above a predetermined level, in a product stream which may trigger an adjustment in the Fischer-Tropsch process will generally be greater than 100 ppm solids, greater than 50 ppm solids, preferably greater than 10 ppm solids, and most preferably greater than 1 ppm solids. When the solids content in the Fischer-Tropsch product is unacceptable, at least one adjustment in the Fischer-Tropsch process may be made to thereby achieve an acceptable or desired level of solids in the product. Examples of such adjustments include separating solids from the Fischer-Tropsch product, routing the product to off-test tankage, recycling the product back to the Fischer-Tropsch reactor, and/or adjusting gas velocity in the Fischer-Tropsch reactor. Separation of solids from the Fischer-Tropsch product may be accomplished by filtration, sedimentation, centrifugation, and/or extraction.

When the Fischer-Tropsch process of the present invention comprises separating solids from the Fischer-Tropsch product and the solids content in the Fischer-Tropsch product is unacceptable, one or more adjustments in the separation may be made. When the separation is accomplished by filtration, the adjustment may comprise changing or cleaning filters. When several filters are used in parallel, filters may be isolated, meaning lines leading to or from a filter may be closed. When the separation is accomplished by sedimentation, the adjustment may comprise changing liquid velocity in the sedimentation zone. When the separation is accomplished by extraction, the adjustment may comprise changing the volume of added solvent and/or the residence time in the extractor.

Thus, the process of the present invention allows one to maintain acceptable solids content and avoid problems downstream through the use of an optical monitoring technique based on light absorption, light scattering, or combinations thereof. The use of the optical technique allows for a more efficient overall Fischer-Tropsch process. As well, the process of the present invention can help avoid potential serious problems in the equipment of customers by monitoring final hydroprocessing products.

The invention will be further illustrated by the following example, which is intended to be non-limiting, but merely illustrative.

EXAMPLE

A commercial jet fuel was used to simulate a liquid product condensed from a Fischer-Tropsch vapor product. Samples of alumina support typically used to make a Fischer-Tropsch catalyst were ground to a fine consistency using a mortar and pestle, and dispersed at various concentrations in the jet fuel. The suspensions were analyzed by three different techniques, each of which operates by measuring a reduction in light transmitted through a sample containing solid particulates. The analytical devices used to make each of the three measurements were:

1) Hach Co. Model 2100 P Turbidimeter;
2) Phase Technology Pour, Cloud, and Freeze Point Analyzer Model No. PSA-70; and
3) Infrared probe made according to U.S. Pat. No. 4,628,204, herein incorporated by reference in its entirety.

The results of the analysis are shown in the table below:

TABLE

| Amount of catalyst added | None | 15 ppm | 182 ppm | 988 ppm | 10,025 ppm |
|---|---|---|---|---|---|
| Visual appearance | Clear | Clear | Cloudy | Cloudy | Very cloudy |
| Turbidity results | | | | | |
| At 15 seconds | 0.58 | 1.15 | 3.60 | 23.7 | 189 |
| At 10 minutes | 0.58 | 0.84 | 2.64 | 13.5 | 35.8 |
| At 16 minutes | 0.56 | 0.76 | 2.31 | 8.3 | 10.3 |
| PSA-70 results | 94.7 | 95.5 | 96.6 | 113.6 | 128.1 |
| IR probe results | 259,120 | 256,660 | 255,020 | 251,740 | 247,640 |

From the foregoing table, it can be seen that visual observation can be used to detect the presence of solids when the concentration is above 15 ppm. Below 15 ppm, the samples appeared clear. Even above 15 ppm, it is difficult to quantify the solids content using visual observation.

The turbidity tests showed that solids below 15 ppm could easily be detected. The IR probe was also very sensitive and detected solids in the 0–15 ppm range. The Phase Technology analyzer showed a more pronounced response when the solids content was in the 15–100 ppm range than at lower levels. Thus, solids content may influence the technique used to measure the light transmitted through a sample.

Accordingly, analytical devices for use in the practice of the present invention can be calibrated, for example, by mixing known amounts of catalyst with samples and analyzing the samples according to the technique of the analytical device being used, as exemplified in the table above. Once calibrated, the solids content of unknown samples may be determined by analyzing the samples according to the technique of the analytical device being used and comparing the results with the calibration data.

Once calibrated, the analytical devices can be used at various locations in the entire facility to monitor solids content, e.g., on the liquid products derived from the vapor stream, on the direct liquid product taken from the slurry bed reactor (the waxy product), on feedstocks to downstream hydroprocessing units, and on products from downstream hydroprocessing units.

This example illustrates that the solids content in a Fischer-Tropsch product may be measured successfully using optical techniques. According to the methods of the present invention, adjustments as described herein may take effect when the solids content in the Fischer-Tropsch product is unacceptable.

Many modifications of the exemplary embodiments of the present invention disclosed above will readily occur to those skilled in the art. Accordingly, the present invention is to be construed as including all structure and methods that fall within the scope of the appended claims.

What is claimed is:

1. A method for monitoring solids content in a Fischer-Tropsch product, the product being derived from a Fischer-Tropsch process comprising a Fischer-Tropsch reactor, the method comprising:
    a) irradiating the Fischer-Tropsch product with light; and
    b) measuring the light transmitted through the Fischer-Tropsch product to determine the solids content in the Fischer-Tropsch product.

2. The method according to claim 1, wherein the light is measured by a method selected from the group consisting of light absorption, light scattering, and combinations thereof.

3. The method according to claim 1, wherein the solids comprise catalyst fines.

4. The method according to claim 1, wherein the light is measured by an on-line analysis.

5. The method according to claim 1, further comprising the step of making at least one adjustment in the Fischer-Tropsch process when the solids content in the Fischer-Tropsch product is unacceptable.

6. The method according to claim 5, wherein the unacceptable solids content is greater than 100 ppm solids.

7. The method according to claim 5, wherein the unacceptable solids content is greater than 50 ppm solids.

8. The method according to claim 5, wherein the unacceptable solids content is greater than 10 ppm solids.

9. The method according to claim 5, wherein the at least one adjustment in the Fischer-Tropsch process is selected from the group consisting of separating solids from the Fischer-Tropsch product, routing the Fischer-Tropsch product to off-test tankage, recycling the Fischer-Tropsch product back to the Fischer-Tropsch reactor, changing gas velocity in the Fischer-Tropsch reactor, and combinations thereof.

10. The method according to claim 9, wherein separating solids from the Fischer-Tropsch product is accomplished by a process selected from the group consisting of filtration, sedimentation, centrifugation, extraction, and combinations thereof.

11. The method according to claim 1, wherein the Fischer-Tropsch process comprises separating solids from the Fischer-Tropsch product.

12. The method according to claim 11, further comprising the step of making at least one adjustment in the Fischer-Tropsch process when the solids content in the Fischer-Tropsch product is unacceptable.

13. The method according to claim 12, wherein separating solids from the Fischer-Tropsch product is accomplished by a process selected from the group consisting of filtration, sedimentation, centrifugation, extraction, and combinations thereof.

14. The method according to claim 13, wherein separating solids from the Fischer-Tropsch product is accomplished by filtration and further wherein the at least one adjustment in the Fischer-Tropsch process is selected from the group consisting of changing filters, cleaning filters, isolating filters, and combinations thereof.

15. The method according to claim 13, wherein separating solids from the Fischer-Tropsch product is accomplished by sedimentation in a sedimentation zone and further wherein the at least one adjustment in the Fischer-Tropsch process is changing liquid velocity in the sedimentation zone.

16. The method according to claim 13, wherein separating solids from the Fischer-Tropsch product is accomplished by extraction using solvent in an extractor and further wherein the at least one adjustment in the Fischer-Tropsch process is selected from the group consisting of changing the volume of added solvent, changing the residence time in the extractor, and combinations thereof.

17. The method according to claim 11, wherein separating solids from the Fischer-Tropsch product is accomplished outside the Fischer-Tropsch reactor.

18. The method according to claim 9, wherein the Fischer-Tropsch process comprises hydroprocessing the Fischer-Tropsch product in a hydroprocessing unit.

19. A method for operating a Fischer-Tropsch process comprising:
   a) recovering a Fischer-Tropsch product from a Fischer-Tropsch reactor;
   b) determining the cloud point of the Fischer-Tropsch product;
   c) selecting an acceptable solids content in the Fischer-Tropsch product;
   d) calibrating an analytical device that measures light transmitted through the Fischer-Tropsch product to determine the solids content in the Fischer-Tropsch product;
   e) irradiating the Fischer-Tropsch product with light;
   f) measuring the light transmitted through the Fischer-Tropsch product using the analytical device;
   g) determining the solids content in the Fischer-Tropsch product; and
   h) making at least one adjustment in the Fischer-Tropsch process when the solids content in the Fischer-Tropsch product is above the acceptable solids content, wherein the at least one adjustment in the Fischer-Tropsch process is selected from the group consisting of separating solids from the Fischer-Tropsch product, routing the Fischer-Tropsch product to off-test tankage, recycling the Fischer-Tropsch product back to the Fischer-Tropsch reactor, changing gas velocity in the Fischer-Tropsch reactor, and combinations thereof.

20. The method according to claim 19, wherein the light is measured by a method selected from the group consisting of light absorption, light scattering, and combinations thereof.

* * * * *